United States Patent [19]
Carr et al.

[11] Patent Number: 4,614,514
[45] Date of Patent: Sep. 30, 1986

[54] MICROWAVE STERILIZER

[75] Inventors: Kenneth L. Carr, Harvard; James F. Regan, Waltham; Gerald G. Bousquet, Chelmsford, all of Mass.; Robert J. Bielawa, Hudson, N.H.

[73] Assignee: M/A Com, Inc., Burlington, Mass.

[21] Appl. No.: 466,894

[22] Filed: Feb. 16, 1983

[51] Int. Cl.$^4$ ............................................. A61F 7/12
[52] U.S. Cl. .................................... 604/113; 604/28; 604/250; 604/411; 422/21; 141/329
[58] Field of Search ............................... 604/113–114, 604/905, 411, 403, 29, 30, 31, 34, 250, 28; 422/1, 21; 141/329–330

[56] References Cited

U.S. PATENT DOCUMENTS

| | | | |
|---|---|---|---|
| 2,254,994 | 9/1941 | Butland | 604/113 |
| 4,157,723 | 6/1979 | Granzow et al. | 604/905 |
| 4,360,435 | 11/1982 | Bellamy et al. | 422/1 |
| 4,405,315 | 9/1983 | Handt | 604/29 |
| 4,412,834 | 11/1983 | Kulin et al. | 604/29 |
| 4,439,179 | 3/1984 | Lueders et al. | 604/250 |
| 4,439,193 | 3/1984 | Larkin | 604/29 |
| 4,443,215 | 4/1984 | Smith | 604/905 |
| 4,473,369 | 9/1984 | Lueder et al. | 604/29 |
| 4,475,900 | 10/1984 | Popovich et al. | 604/29 |

FOREIGN PATENT DOCUMENTS 2330317  2/1974  Fed. Rep. of Germany ...... 604/114

OTHER PUBLICATIONS

"In Vitro Studies of Surface Sterilization of CAPD Tubing Using UV Light", S. J. Joshi et al. *Kidney International*, vol. 19, No. 1, Jan. 1981.

Primary Examiner—C. Fred Rosenbaum
Assistant Examiner—Gene B. Kartchner
Attorney, Agent, or Firm—Wolf, Greenfield & Sacks

[57] ABSTRACT

A microwave sterilizer for sterilizing a connector or coupling that interconnects a first conduit from a source of liquid to be infused into a living body to a second conduit implanted in the body. The apparatus of the invention comprises a housing having first and second members forming a guided wave structure adapted to be removably closed around the coupling or connector and further including first and second clamping means. The clamping means are adapted to clamp respective conduits and are operable to isolate a charge of the liquid within the connector. A microwave source is used to generate energy which in turn is coupled to the guided wave structure to cause heating of the liquid charge to a temperature level to cause sterilization so as to destroy substantially all form of bacteria therein. After a predetermined heating sequence, the apparatus is released and the bag side clamping means is first released so as to pass the sterilized charge of liquid into the source or bag.

15 Claims, 10 Drawing Figures

MICROWAVE STERILIZER

BACKGROUND OF THE INVENTION

The present invention relates in general to a microwave sterilizer and pertains, more particularly, to a microwave sterilizer employing a balanced coaxial transmission line for providing intense heating for sterilization.

At present, patients who are required to connect to dialysis or the like equipment use a standard coupling connection. It has been found that bacteria, such as staphylococcus bacteria may exist at the coupling. Presently, patients have to be quite careful in making sure that the connection is made without making direct contact with the members that are intercoupled. Another problem, particularly for the elderly and those that lack manual dexterity is that they are required to provide a mating of the connector, either with or without assistance, that interconnects the source of liquid to the living body. Additionally, many patients are diabetic and may have limited vision which makes this interconnection difficult.

Accordingly, it is an object of the present invention to provide a microwave sterilizer for sterilizing the conduit coupling or connector that couples from a liquid source in which the liquid is infused into a living body. For example, the system with which the microwave sterilizer may be used is with a technique called "continuous ambulatory peritoneal dialysis" or CAPD for short. CAPD means, quite literally, ambulatory dialysis employing the peritoneum, the internal lining of the abdominal cavity, as a filtering membrane. However, it is also understood that the concepts of this invention also apply to other techniques for infusing a liquid into a living body from a source of the liquid. For example, the concepts of the invention may also be applied in intravenous infusions.

Another object of the present invention is to provide a microwave sterilizer apparatus which provides for the mating of the connector or coupling with the mating preferably taking place concurrently with the clamping of the conduit on either side of the connector or coupling so as to isolate a charge (small volume) of the liquid within the connector or coupling. The mating and clamping is followed by the application of heat by means of a guided wave member adapted to enclose the coupling or connector.

Still another object of the present invention is to provide a microwave sterilizer in accordance with the preceding objects and which is relatively simple in construction, very safe in operation, extremely effective in providing the necessary sterilizing heat, and which is readily operable by the elderly, those with impaired vision, or those lacking manual dexterity.

SUMMARY OF THE INVENTION

To accomplish the foregoing and other objects of this invention, there is provided a system for infusing a liquid into a living body by means of a coupling or connector that intercouples a conduit from the source of the liquid which may, by way of example, be a saline solution to a conduit implanted in the body. In accordance with the invention, apparatus is provided for sterilizing the coupling or connector with this apparatus comprising a guided wave member adapted to enclose the coupling and means for heating by excitation of the guided wave member to heat an initial charge of the liquid to an elevated temperature for a time long enough to destroy bacteria. The apparatus preferably comprises a housing including first and second members forming the aforementioned guided wave member arranged to be removably closed around the connector or coupling. There is also provided first and second clamping means on opposite sides of the coupling or connector and means to operate the clamping means to isolate a charge of the liquid within the connector. The clamping means is also operated to be subsequently released after the sterilization has been completed. In this connection, the clamps are released in sequence to first discharge any liquid into the source rather than the body. In the preferred construction one of the guided wave members is in a fixed position in the housing while the other member is pivoted relative to the one member to open and close the guided wave member. It is also preferred to employ as part of the apparatus, a carriage in the housing for supporting one of the conduits and means for supporting the other conduit in a fixed position and also further including means for operating the carriage to cause the conduits to be joined by virtue of mating the coupling or connector.

In accordance with the method of this invention, there is provided, for the infusing of a liquid into a living body, in a process which requires the initial step of coupling a conduit from a source of the liquid to a conduit implanted in the body. The method steps include the steps of, following the coupling, holding an initial charge of the liquid in the conduit bridging the coupled ends of the conduit, heating the initial charge to an elevated temperature for a time long enough to destroy bacteria, such as staphylococcus bacteria and then releasing the liquid into the source. The method preferably also includes the step of temporarily fixing the coupled ends in a microwave heating enclosure and heating the initial charge in the enclosure. By virtue of the connector or coupling being closed, this means that the liquid is put under elevated pressure while heating to intensify the heating and to bring the temperature up to a proper level to cause sterilization.

In accordance with still a further aspect of the present invention there is provided an improved coupling or connector which comprises a hollow male member connected to one of said conduits and a hollow female member connected to the other of said conduits. These conduits are the ones for infusing a liquid into a living body including a conduit from the source of the liquid and a conduit implanted in the body. The male and female members are adapted to engage and the male member is provided with a spike end entering the female member. The female member has an inner diameter along a section thereof greater than the diameter of the spike end so as to provide an annular space about the spike end to accommodate the liquid providing a reservoir charge of the liquid about the spike end capable of being heated for sterilization thereof.

BRIEF DESCRIPTION OF THE DRAWINGS

Numerous other objects, features and advantages of the invention should now become apparent upon a reading of the following detailed description taken in conjunction with the accompanying drawing, in which.

DETAILED DESCRIPTION

Figure 1:
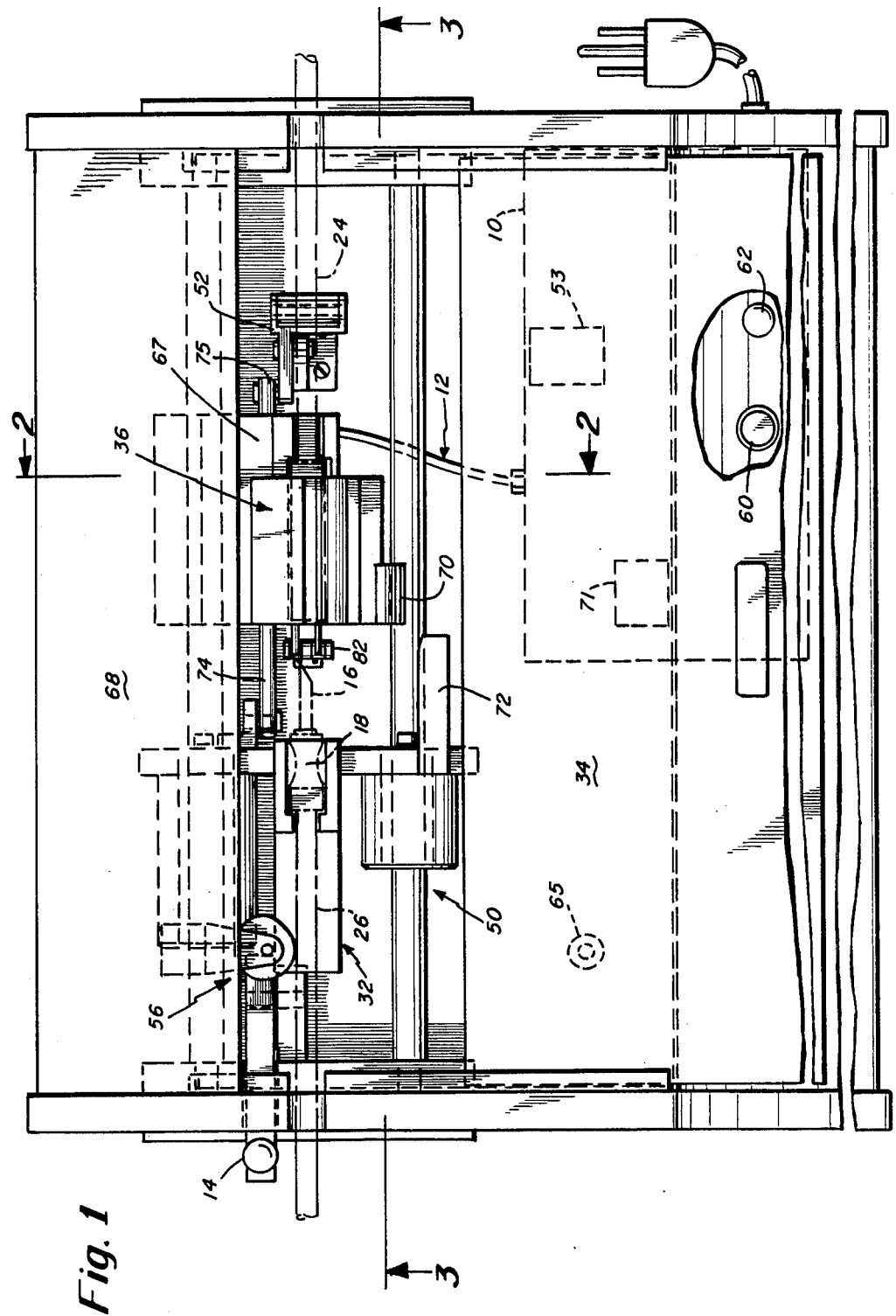
FIG. 1 is a top plan view of the apparatus of this invention with the door open and showing the coupling tubes in phantom.

Referring now to the drawings, there is shown a complete apparatus for the microwave sterilizer of this invention. A substantial part of this apparatus is for carrying out mechanical functions such as the mating of the connector parts and the clamping of the conduits. As far as the sterilization is concerned, this is accomplished by means of the microwave sterilizer which broadly is comprised of a solid state microwave source 10 coupled to a short coaxial cable 12 (see FIG. 2). With regard to the transmission line defined by the curved conductors 42 and 43, the loss, or attenuation is determined by the microwave characteristics of the loading (i.e. the liquid contained within the connector) forming a lossy structure. As indicated previously, a mechanism is provided for the mechanical mating of the two connector parts. The mechanism to be described in further detail hereinafter also allows for the introduction and confinement of the liquid in the area of mating or in other words, in the coupling or connector itself.

In accordance with the present invention and the apparatus and method described herein, the sequence and duration of operation is significant. The general sequence of steps is the alignment and mating of the conduit or tubing, the clamping of the conduit or tubing, activation of the microwave source for a predetermined heating period and then release of the clamping in a predetermined manner to be described hereinafter. By way of example, in the application associated with CAPD patients, pushing of an actuating lever such as the lever 14 (FIG. 3) shown in the drawings combines the spike 16 of the male connector 18 with the female connector 20. This action also causes a piercing of the diaphragm 21 which has been placed between the separate parts 22 and 23 comprising the female member. The diaphragm 21 is used to seal the connection to the source of the liquid. Note the connection of the female member 20 to the conduit 24. Similarly, the male member 18 couples to the conduit 26. It is also noted that the female member preferably has a sealing O-ring 27.

Figure 4:
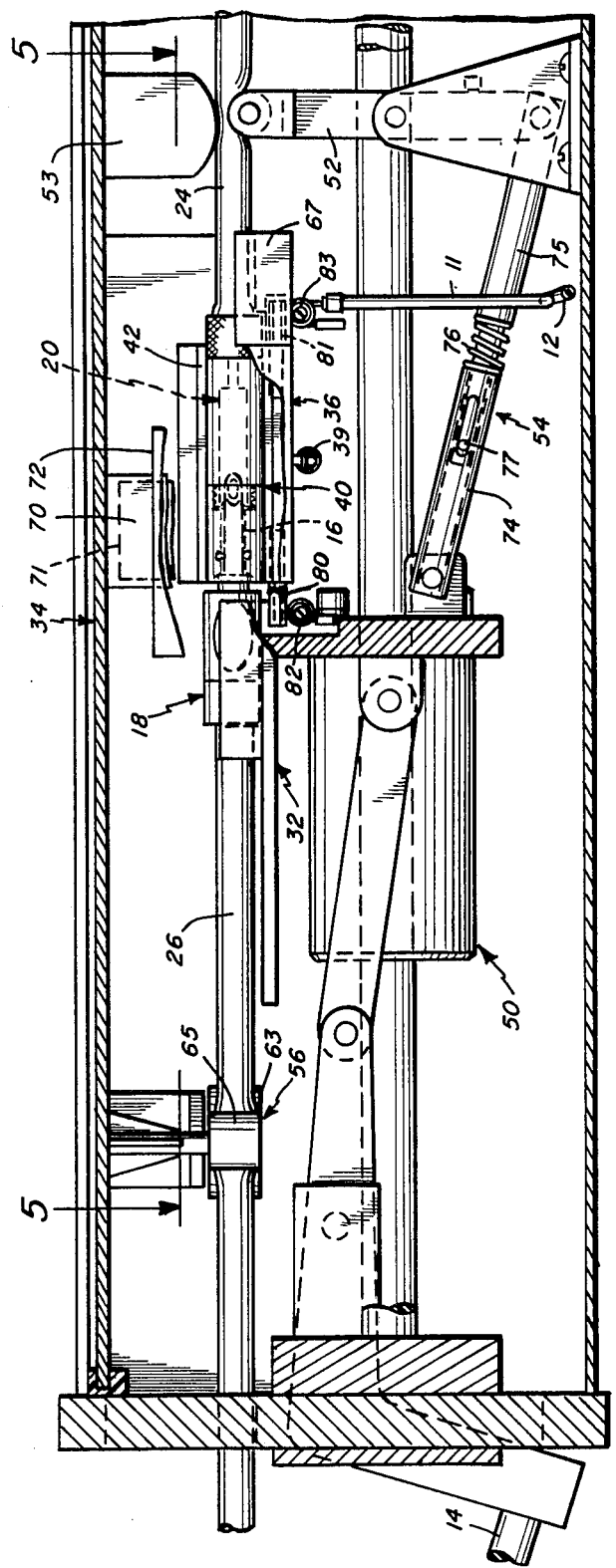
FIG. 4 is a second view of the invention in a view similar to the cross-sectional view of FIG. 3 but with the operating lever being moved to the coupling engaging position.

On the return motion of the lever 14, such as illustrated in FIG. 4, the clamps are opened with the clamp on the bag side opening first and just prior to reaching the full return stroke position, the clamp on the patient's side opens. This is to make sure that the liquid that has just been heated in the connector does not pass back into the body, but instead is discharged, should any discharge occur, back into the reservoir or bag that is used for the liquid. This operation is relatively simple and it is safe for the patient to use.

In brief summary, the sequence of operation is as follows:

1. The patient prepares the new bag containing the solution and positions the male and female connector members along with the silastic tubing into the fixture located in the apparatus. The silastic tubing is represented by the conduits 24 and 26, previously mentioned.

2. The patient locates and positions the spike 16 along with its associated conduit or tubing 26 into a transfer nest 32.

Figure 5:
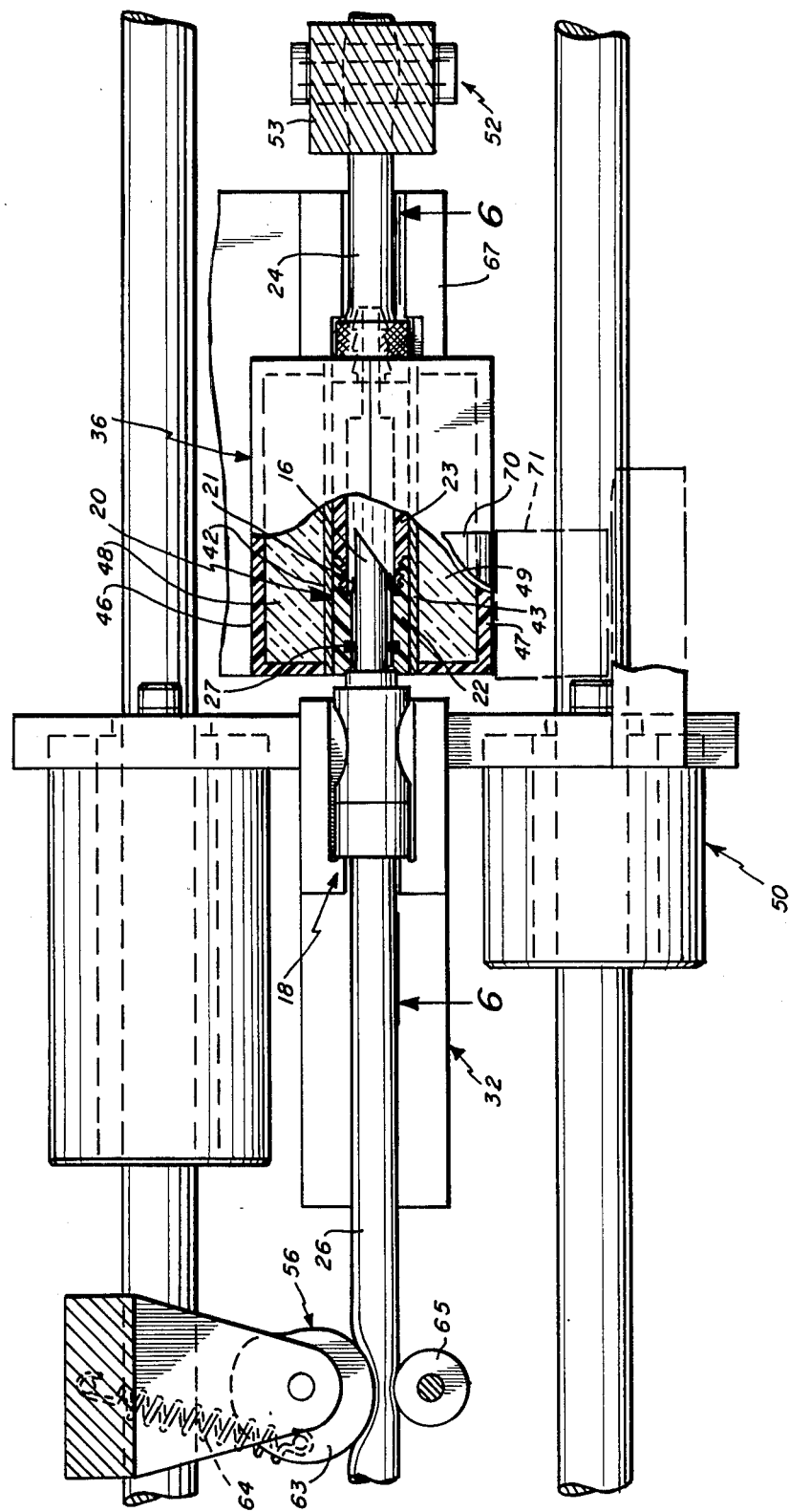
FIG. 5 is a cross-sectional view taken along line 5—5 of FIG. 4 showing further details of the heating blocks.

3. The patient then closes the top cover 34. This motion engages the pivotal heater block 36 (see FIG. 7) so as to close both the heater block 36 and the stationary heater block 38 about the connector 40 which comprises the male member 18 and the female member 20. This motion also moves the fixed piece or pinch block 53 into position over the pivot member 52 with the tubing 24 in between, and positions pressure roller 65 to slightly pinch tube 26 against eccentric cam 63 to provide friction between tube 26 and eccentric cam 63 so actuating lever 14 results in the tubing 26 rotating cam 63 counterclockwise, as illustrated in FIG. 5, to pinch off the tubing 2.

4. The patient then actuates the lever 14 which clamps off both tubes 24 and 26, engages safety latch 72, and transfers the spike 16 into the female connector 20. This pierces the diaphragm 21. A proper seal is provided to protect from liquid leaking by means of the O-ring 27.

5. The patient then activates a switch for exciting the microwave source 10 and the process runs until completion as either controlled by a timer or by sensing a temperature of 138° C.

6. Upon completion of the heating cycle, a light and/or sound is preferably generated to indicate to the operator that sterilization has been completed.

7. The patient then retracts the lever 14 and the tubing is unclamped in sequence with the tubing 24 being unclamped first, followed by unclamping of the tubing 26.

8. The top cover or door 34 is then opened. The heating blocks 36 and 38 have a spring 39 (see FIG. 7) associated therewith that normally pivots the pivotal heater block to its open position so that when the door or cover is opened, then the heater blocks are also opened, or in other words, the guided wave member is opened so that the connector or coupling 40 may be removed therefrom.

Figure 2:
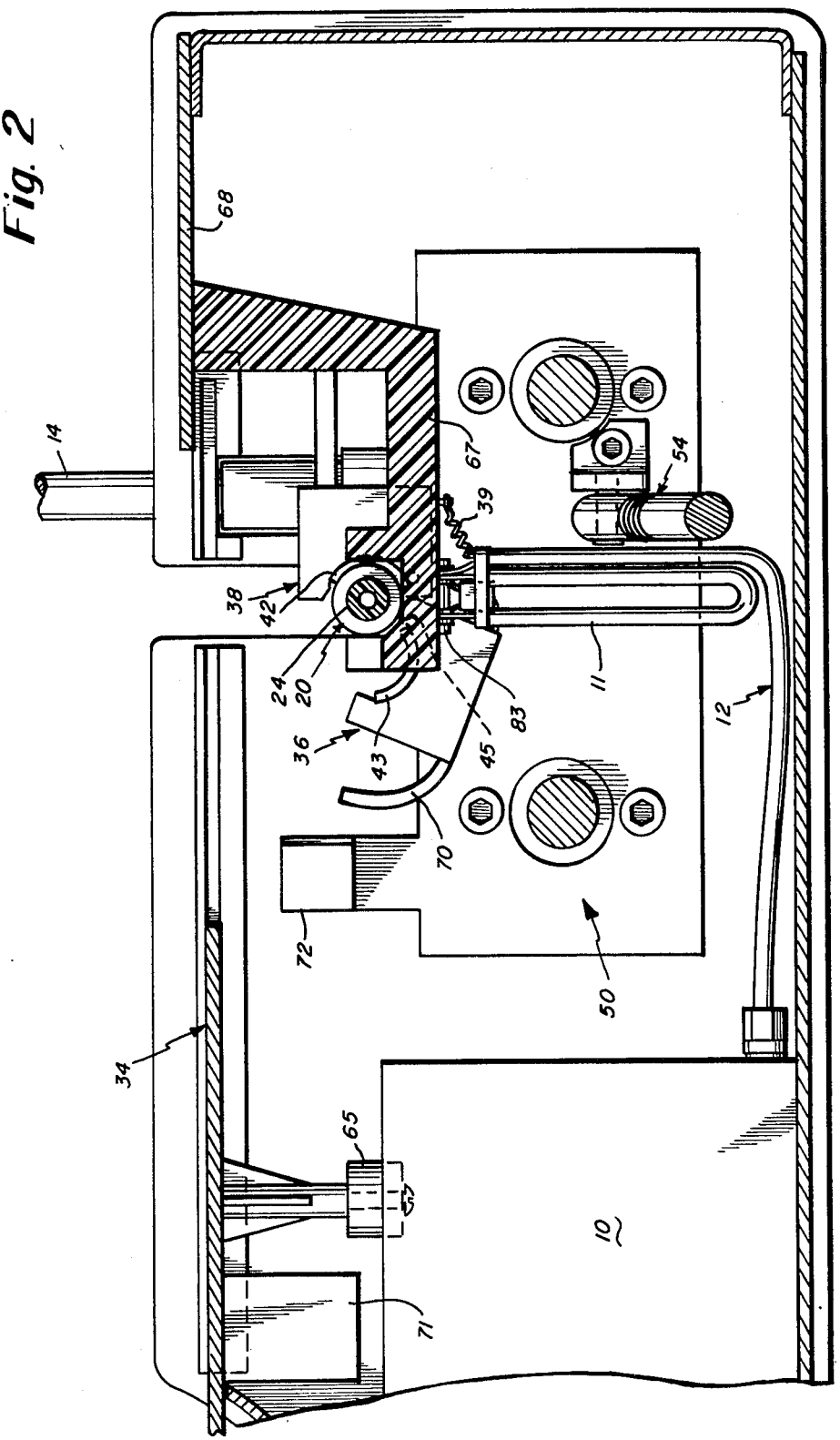
FIG. 2 is a cross-sectional view taken along line 2—2 of FIG. 1 showing the apparatus in its cover-open position.

As illustrated in FIG. 2, there is a two-wire transmission line configuration shown in FIG. 2 in the open position of the cover 34. Also refer to the detailed drawing of FIG. 7 which shows the curved conductors 42 and 43. Each of these may be made of stainless steel to minimize heat transfer from the liquid. A rotary hinge joint 45 is provided to permit the pivotal movement of the heater block 36. Each of the heater blocks preferably also includes respective housing members 46 and 47 and internal insulation 48 and 49. The outer members 46 and 47 may be of a plastic material and the insulation is adapted to maintain the heat concentrated within the connector 40.

FIG. 2 also shows the balun 11 for converting from a unbalanced to an balanced configuration. Also shown are the end tuning variable capacitors for proper tuning of the guided wave structure.

Figure 3:
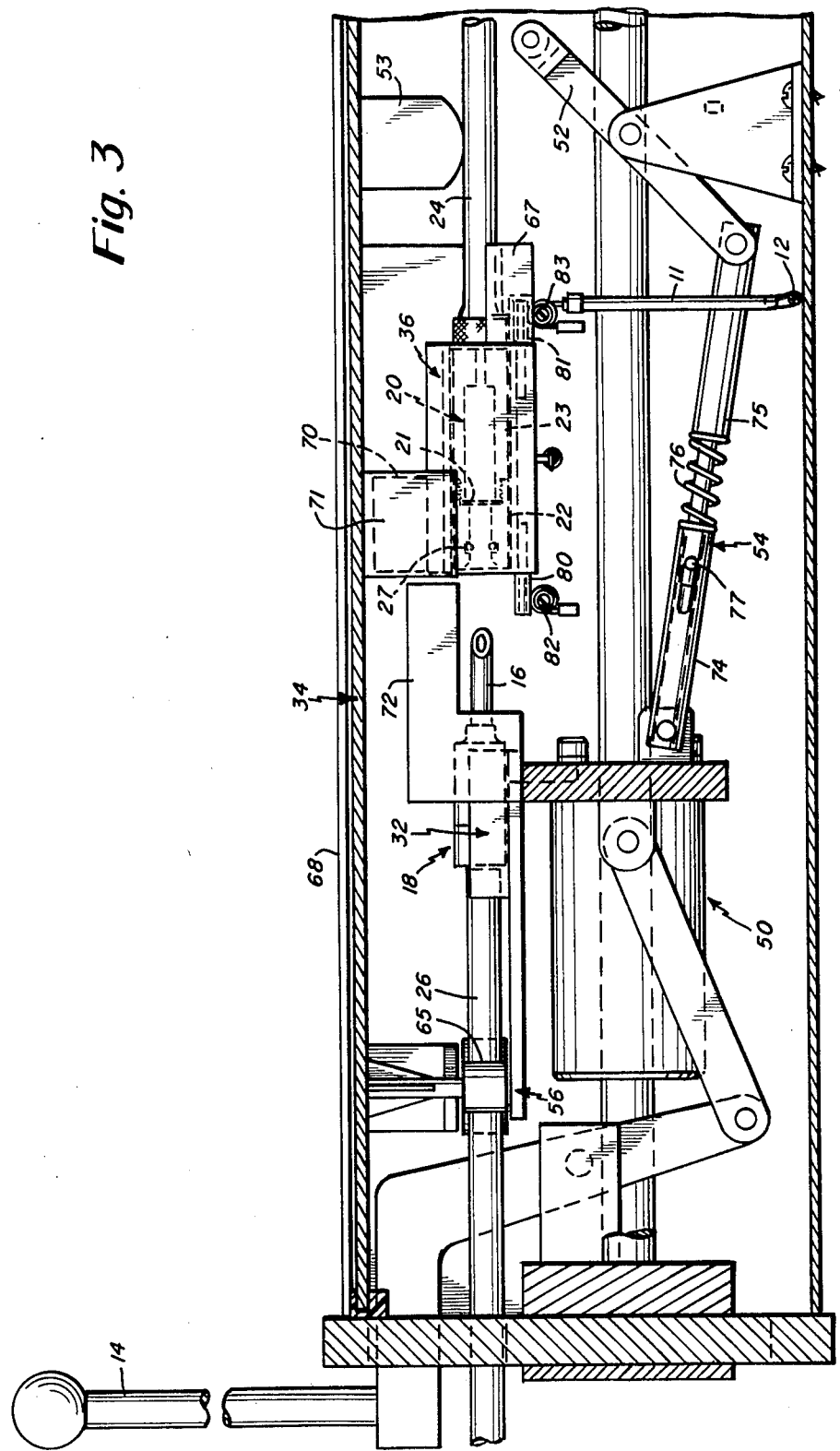
FIG. 3 is a cross-sectional view taken in the opposite direction along line 3—3 of FIG. 1 showing the apparatus with the door closed and lever unactivated.

With regard to the mechanism for carrying out the mating of the connector and the clamping functions, reference is made to FIG. 3 which shows a carriage 50 which supports the transfer nest 32. The carriage 50 is adapted for lateral movement under control of the lever 14. When the lever is in the upper position of FIG. 3, then the carriage is to the left and when the lever 14 is moved to its downward position, then the carriage traverses to the right so as to provide the aforementioned mating. FIG. 3 shows the position of the lever in the unmated state. FIG. 4 shows the lever having been moved to cause the mating of the connector 40.

Figure 8:
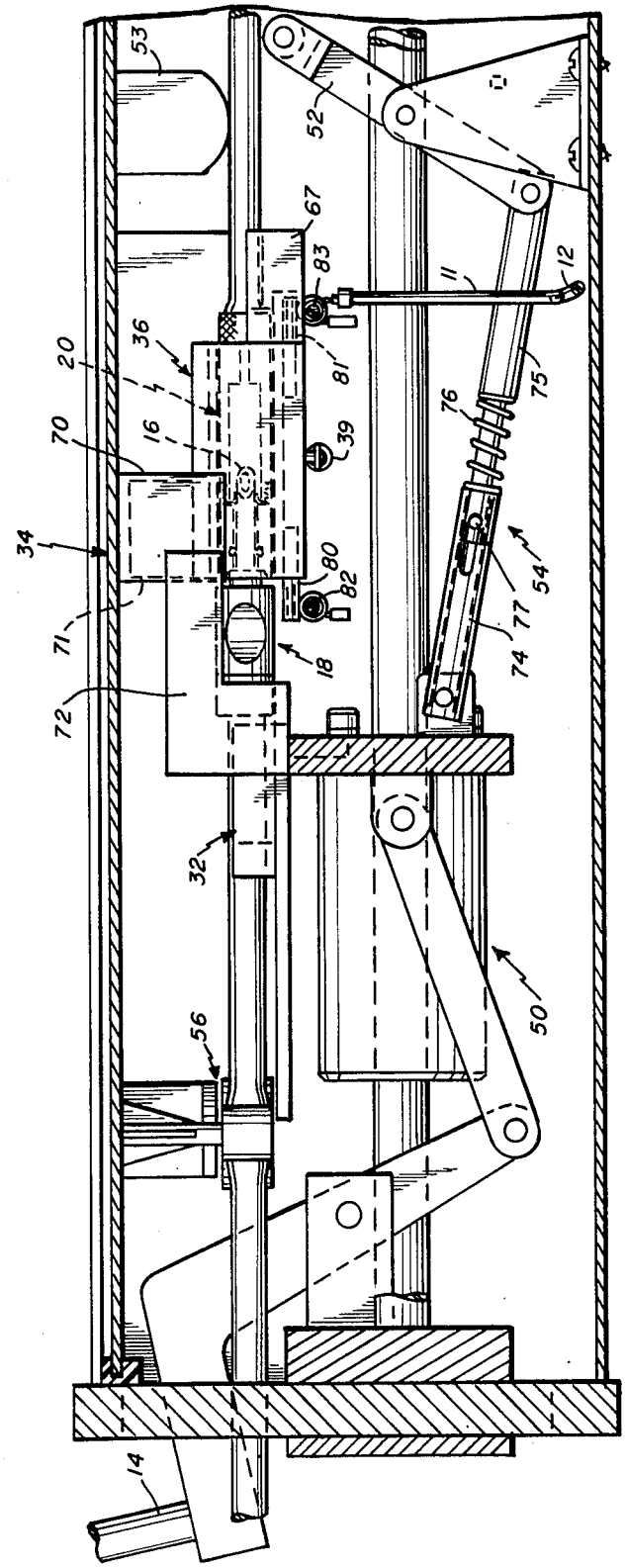
FIG. 8 is a view similar to the cross-sectional views of FIGS. 3 and 4 showing a release sequence.

With regard to the clamping action, it is noted that the conduit 24 is clamped or crimped by means of pivot member 52 co-acting with pinch block 53. Pivot member 52 is operated from the carriage 50 by means of the connector 54 (FIG. 8). There is also provided a clamp member 56 also operated by means of lateral movement of the carriage 50. The clamping member 56 may be of the eccentric type that provides for a clamping of the conduit or tubing 26. As indicated previously, these clamps operate so that during the unclamping sequence after the water in the connector 40 has been heated, the clamp member associated with the tubing 24 is released first. This is the conduit that couples back into the bag and it is desired to couple any heated liquid back into the bag rather than into the patient. That is why the clamping member 56 is finally released at a later time after release of the other clamping member associated with conduit 24.

The microwave structure that has been described, including the solid state source, is quite compact, efficient, and safe to operate. With this arrangement, a small amount of liquid may be heated rapidly at a relatively low power level. If, for example, one assumes a cylinder of water one centimeter in diameter by five centimeters long, then:

$$Vol = \frac{\pi d^2 h}{4}$$

$$= 3.93 \text{ cu cm}$$

Mass, $M = Vol \times 1 \text{ gm/cm}^2$ $$= 3.93 \text{ gms}$$

Energy, $Q = Mc \Delta T$ where $c$ = specific heat $Q = 3.93 \text{ gms} \times c = \text{spec. heat in 1 cal/gm}° \text{ C.} \times 80° \text{ C.}$ $Q = 315 \text{ Calories}$ Power, $P = \frac{4.18 Q}{t}$ assume $t = 5$ min. or 300 sec.

$$P = \frac{4.18 (315)}{300}, \text{ or } 4.39 \text{ watts}$$

Figure 9:
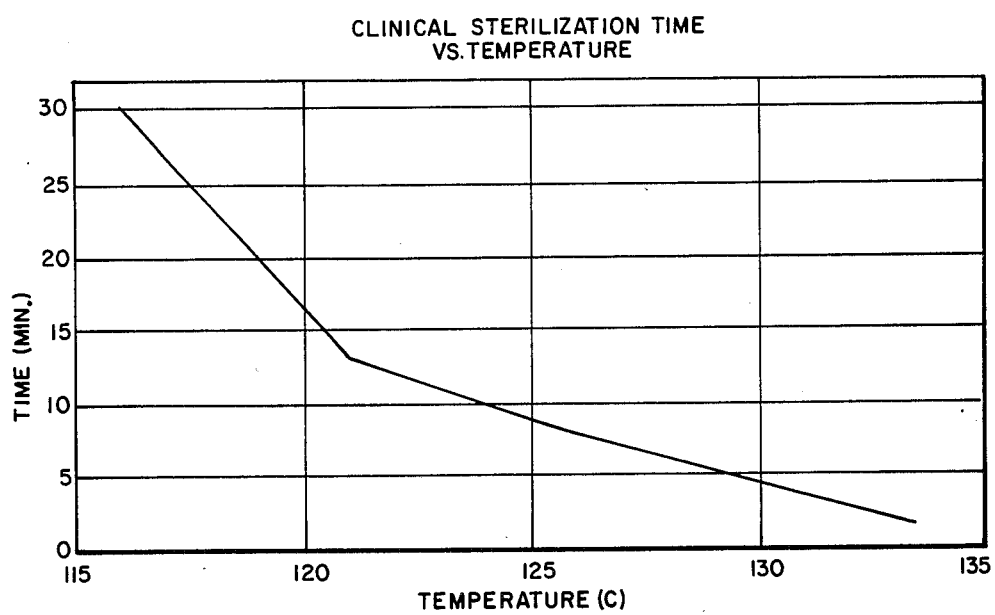
FIG. 9 is a graph of clinical sterilization time versus temperature in connection with the apparatus of this invention.
Figure 10:
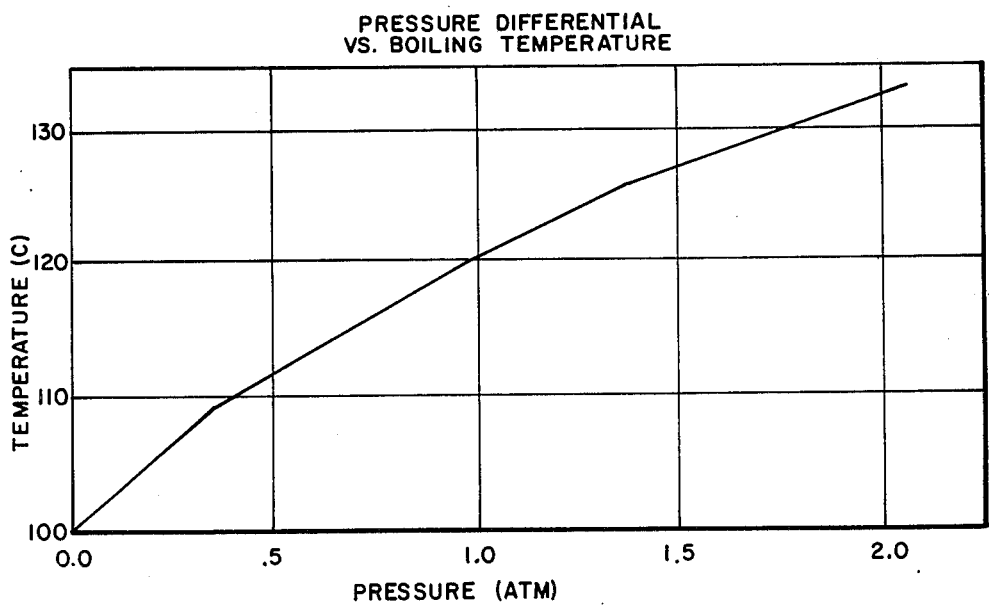
FIG. 10 is a graph of pressure versus temperature in connection with the apparatus of this invention.

The connector 40 which includes the female member 20 and the male member 18 is uniquely constructed so that the inner diameter as represented by the dimension B is significantly greater than the diameter of the spike 16 as represented by the dimension A. See FIG. 6 for dimensions A and B. This thus provides a liquid accommodating space of annular construction surrounding the spike 16. This space within the female member 20 provides for a charge of liquid therein surrounding a substantial portion of the spike 16, which liquid is heated in accordance with the invention to provide sterilization. Because the liquid is trapped in the connector by the aforementioned clamping means, and is thus held at a constant volume, there is a resulting pressure increase which will allow the liquid temperature to rise well above the normal 100° C. boiling point of water. In fact, as indicated in the graph of FIG. 9 which is a plot of clinical sterilization time vs. temperature, the temperature may reach in excess of 138° C. Also note the graph of FIG. 10 which is a graph of temperature vs. pressure.

The connector 40 and associated tubing 24 and 26 has low attenuation at the microwave frequency range employed. In this connection, the microwave source may be at a frequency of 915 MHz. However, the liquid contained within the microwave structure is highly absorptive. The balanced transmission line comprised of conductors 42 and 43 (FIG. 7) may be terminated in either a short circuit or open circuit. In this way the transmitter power not absorbed by the liquid initially is reflected, or directed back, into the lossy liquid. The loss of the structure is adequate to present a proper match to the microwave transmitter.

The 915 MHz solid state source 10 preferably operates from a typical voltage supply of 12 volts, allowing safe operation from either battery or low voltage power supply. The output of the 915 MHz solid state source is approximately 15 watts. With this low power operation the device is thus compact, efficient and safe in operation.

Sterilization tests that have been performed verify that the sterilizer, or microwave autoclave, is capable of clinically sterilizing a connector in a reasonably short time using only a relatively low level of power. Cultures have been prepared (i.e., bacteria including spore form) in a supporting media conducive to their growth. Bacteria included staph, aureus, pseudomonas, aeruginosa, candida, albicans, and bacillus stenrothermophilus. The culture media included 5% sheep blood agar, chocolate agar with 5% sheep blood, trypticase soy broth, and Columbia broth. These samples were placed in the microwave sterilizer for 4.5 minutes at an incident, or transmitter, power level of 15W. During this period of time the temperature of the solution exceeded 138° C. The temperature of the solution within the plastic test section was determined through the use of heat sensitive indicators. The various solutions were examined at the end of seven days and it was determined that the solutions were sterile (i.e., all forms of bacteria, including spores, were destroyed.)

Figure 6:
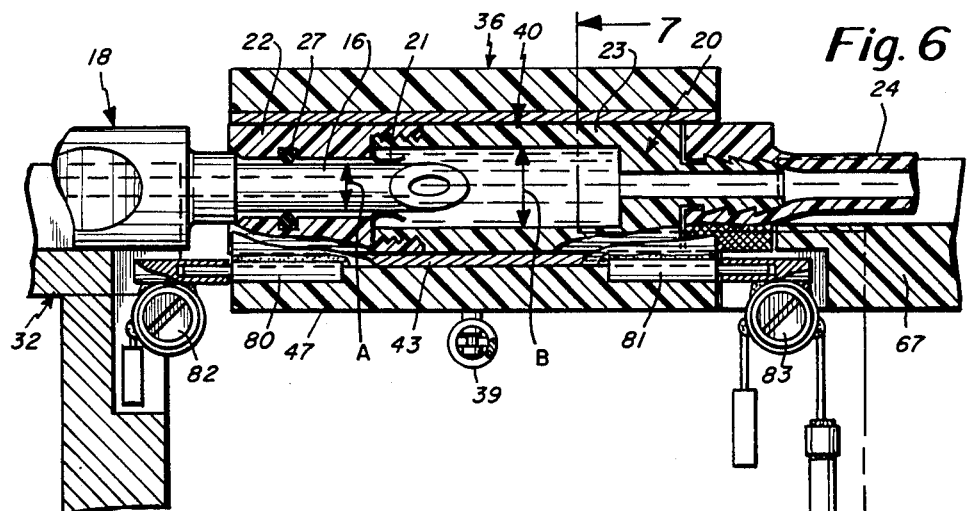
FIG. 6 is a cross-sectional view taken along line 6—6 of FIG. 5.

During sterilization it is possible that air may be trapped in the space about the spike between the spike and the mating female connector. With reference to FIG. 6 this may be in the area about the spike 16 at the left end of the female connector part 23. The trapped air with associated surface tension may prevent the flow of water into this air pocket in the gap or space about the male spike.

In connection with FIG. 6 one can also assume a radius R1 for the inner diameter of the female member and a radius R2 for the radius of the spike. These are the radii that determine the aforementioned gap or space. For any given geometry (i.e. for every radius ratio of R1/R2) there exists some pressure differential wherein the pressure differential is the difference in pressure between the liquid bearing portion and the air bearing portion of the volume, which will overcome the surface tension. It is preferred to use nominal values of pressure differential and one can assume a relatively small value of pressure differential to assure that small pressure fluxuations produced as the water begins to boil are significant to overcome the surface tension associated with a trapped bubble or volume of air. The pressure fluxuation is in the order of 0.5 psi for the formation of a steam bubble. Therefore, one should choose the geometry such that the pressure differential is equal to 0.5 psi so that this value is sufficient to overcome the surface tension.

Determining the geometry involves a procedure that converges on the largest radius ratio (R1/R2) that is capable of supporting the surface tension when the pressure in the water is 0.5 psi higher than in the air bubble.

Assuming zero viscosity, this ratio is:

$$R1/R2 = 1.008$$

Any ratio above this number will not support the surface tension, and water will flow freely into the air pocket which is desired.

Hereinbefore, there has been a brief description of the apparatus and of the sequences of operation. There now follows a more detailed description of the apparatus and operation. Thus, in FIG. 1 there is shown a plan view with the door or cover 34 open showing the tubes 24 and 26 in phantom. In FIG. 1 in the cut away portion of the door 34, there is shown the start heater button 60 and the time-out light 62. FIG. 1 also shows the eccentric type clamp 56. This is in the form of a pinch valve operating with an eccentric cam 63 (FIG. 5) and associated spring 64. The clamping member or valve is indexed by the extension spring 64 shown in phantom in FIG. 5. FIG. 5 also shows the pressure roller 65 associated with the cam 63. The eccentric roller form of clamp is mounted in a fixed position while the pressure roller is mounted on the sliding door 34. When the door 34 is closed, the pressure roller pushes the tubing 1/32 of an inch into and toward the eccentric cam 63 in order that friction will rotate the cam counter clockwise when the carriage is moved to the right in FIG. 1. In FIG. 5 there is shown the position in which the clamping member 56 is in its pinched position. The surface of the cam 63 is constructed so that one inch of carriage travel pulls the tubing and rotates the cam from its index position through an increasing radii until creating a ¼ inch pinch of the tubing. This pinch valve arrangement once activated, stays pinched onto the tubing until the door is opened at the very end of the sequence, pulling the pressure roller back and releasing the binding action on the cam. This allows the extension spring 64 to index the cam 63 back clockwise to its narrowest point in relationship to the tubing in readiness for the next cycle. The cam also is made so that once one inch of travel has pinched the tube, any further rotation is a constant pressure. This is noted in FIG. 5 by the constant diameter of the cam 63 about the majority of its radius.

FIG. 2 is a cross-sectional view taken along line 2—2 of FIG. 1 showing the cradle arrangement for the female (bag end) end of the tubing. This cradle 67 is suspended from the fixed portion of the cover as represented by the top wall 68. In the view of FIG. 2 the heater blocks 36 and 38 are shown just behind the cradle 67. In FIG. 2 the block 36 is biased open under the bias of the extension spring 39 which is partially hidden in the view of FIG. 2 behind the balun 11 and associated variable capacitors. The variable capacitors are used for tuning as mentioned previously. It is noted that the block 36 carries at its upper left corner, a curved protrusion 70. This protrusion is adapted to be contacted by the block 71 mounted to the far left underside of the sliding door 34. This contact occurs as the door is slid closed or slid toward the right in FIG. 2. Thus, as the cover is closed, this block 71 engages the protrusion 70 to close the guided wave member against the spring tension of spring 39. The safety latch 72 is part of the bearing mounting plate and, when activated by the handle or lever 14 which slides the carriage, comes forward behind the block 71 after the sliding door is closed. As is evident from the cross-sectional view of FIG. 3, the safety latch 72 prevents the door from being opened by as little as 1/16th of an inch travel of the carriage. FIG. 2 also shows the power source 10 to the left having its output coupling by way of transmission line 12 to the guided wave member.

FIG. 3 is a front elevation view in cross-section taken along 3—3 of FIG. 1. The pinch rollers, one of which is the aforementioned eccentric cam, is shown with one being in front of the other and with the tubing 26 sandwiched therebetween. Note in FIG. 3 the pressure roller 65. The linkage between the bearing mounting plate and the right hand side pinch valve as represented by the linkage 52, is a lost motion linkage as represented by the connector 54 which is comprised of a spring biased arrangement providing limited slip of ½ inch. This linkage includes a left hand member 74 which is a hollow tube with a slot milled in it. The right side of the linkage is a rod 75 with a reduced neck with a spring 76 slid over the neck and a roll pin 77 inserted through a hole in the neck and through the slot. As the handle 14 is brought down, and the carriage moves from left to right, the linkage is pushing the pinch valve shut via the spring compression with a force of 4 lbs. spring pressure. The roll pin 77 does not bottom out on the push stroke. Instead, on the return stroke of the carriage, it does bottom out in the slot after ½ inch or less of movement and it then pulls the pinch valve on the bag side open. It is also noted that the limit lug on the pinch arm bracket which in FIG. 4 is shown in phantom prevents the arm from going over center in relation to the pinch block 53 which is mounted on the sliding cover.

FIG. 4 shows the cover 34 closed with the safety latch and part of the rotating heater block partially cut away. The heater block is closed in this position and the safety latch 72 (FIG. 2) engages. It is noted that the handle 14 is in its downward position thus causing both of the pinch valves or clamping members to operate. This also causes the spike (needle) 16 to pierce through the diaphragm 21. The sliding door is thus in a locked position.

FIG. 5 shows the heater block partially broken away to show the details of the inserted spike 16. FIG. 5 also shows the operation of the eccentric type clamping member and also shows in an overlying relationship the clamping at the bag side as represented by the interaction of the pivot member 52 with the finch block 53. In phantom, in front of the rotating half of the heater block is the activating member 71 that closes the pivotal heater block 36. FIG. 5 also shows partially broken away and partially in phantom, the aforementioned safety latch which is part of the bearing plate assembly.

FIG. 6 shows longitudinally the heater block partially broken away. FIG. 6 also shows the details of the hinging including hinge pins 80 and 81 which facilitate pivoting of the pivotal heater block 36. FIG. 6 also shows the spring 39 and part of the cradle 67. Also shown are the tuning capacitors 82 and 83 and a portion of the input transmission line 12.

Figure 7:
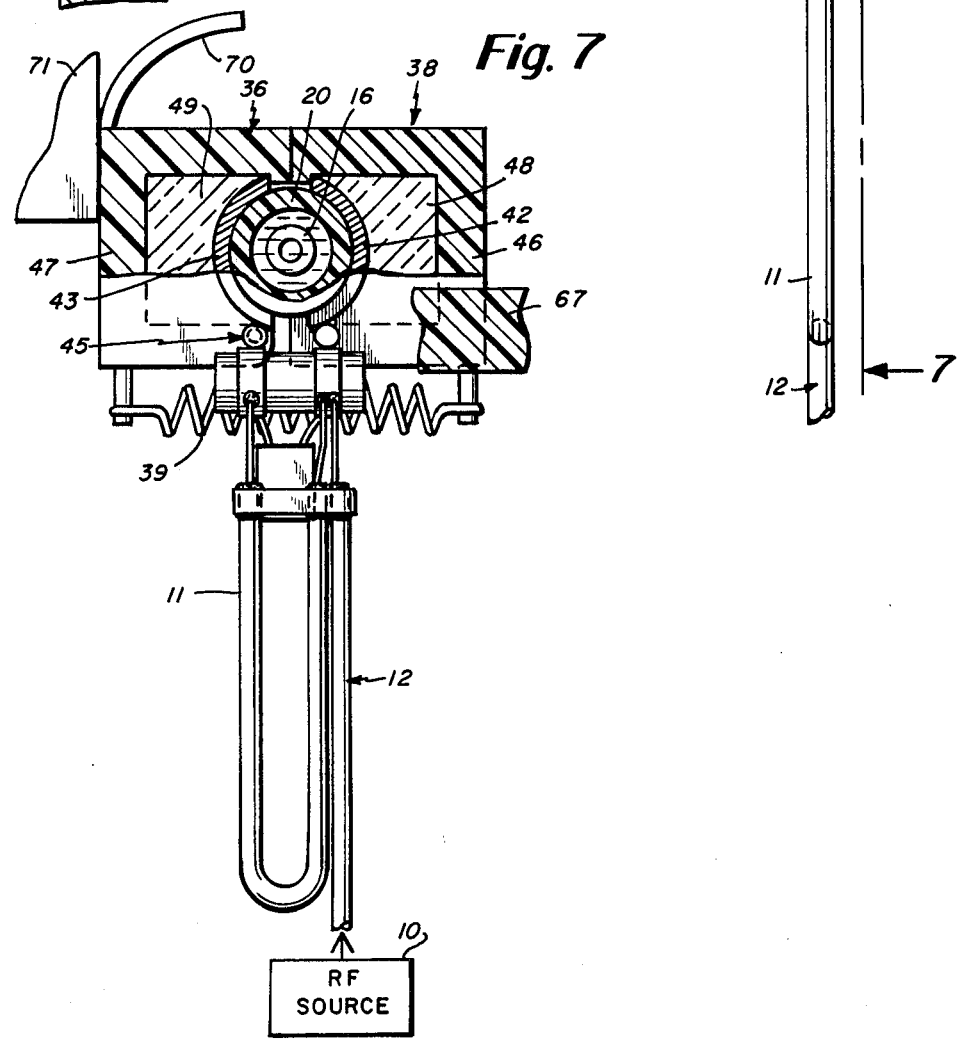
FIG. 7 is a cross-sectional view taken along line 7—7 of FIG. 6 showing further details of the heating block.

FIG. 7 is a cross-sectional view taken along the cross-section line 7—7 of FIG. 6. In this view the cradle 67 is mostly broken away to show details of the hinge 45 and further details of the variable tuning capacitors or tuning elements. The biasing spring 39 is shown at the bottom of the heater block. It is also noted in FIG. 7 that there is shown the actuating block 71 that closes the movable heater block 36. FIG. 7 also shows the protrusion 70 that cooperates with the block 71. The end of the male spike 16 is seem inside of the female connector with the liquid thereabout in readiness for heating.

FIG. 8 shows the release sequence. The view of FIG. 8 is the same cross-sectional view as shown in FIGS. 3 and 4. In this position, the lever or handle 14 has partically raised again. This action is taken after the heating sequence has terminated. This action moves the carriage 50 back to the left leaving the male and female connector members together. It is noted that the pinch valve or clamp member on the right side, namely the pivot member 52 has been released. However, the left clamping member 56 is still shut and remains shut until the safety latch is released on the last bit of travel on the carriage, which leaves the door 34 free to move under bias of spring 39 and resiliency of walls of the tubing 26.

In summary, the operation is as follows. The user opens the cover 34 by sliding it forward. This opens the 7 inch wide cover to expose a gap of about 3½ inches thus exposing the cradle and transfer nest. The heater block is also open. The user then places the male and female connectors in their respective cradles and slides the door closed. This closing of the door operates the heater block 36 and pushes the pressure roller 65 against the tube on the patient tube side so that a frictional drag is created on the rotating cam pinch valve, and locates pinch block 53 over pivot member 52.

The user then starts to pull the handle 14 down. The first 1/16 inch travel of the carriage locks the door closed. The carriage continues on toward the heater block and after one inch of travel, the patient side pinch valve, namely the one including the eccentric cam 63 closes off the tubing completely and evens out by virtue of the constant diameter so that no more pressure is exerted during the final half inch of travel of the carriage. The lost motion linkage 54 meanwhile is closing the bag side tubing under spring tension until it closes the tube completely with spring pressure. This occurs when the spike is approximately ⅛ inch away from piercing the diaphragm. The carriage continues piercing the diaphragm and going well past so that the diaphragm will not interfere with flow. The spring pressure builds up to approximately 4 lbs. of pressure against the pinch valve even on the bag side. The handle rides over center of the linkage. The user then pushes the heater start button. This activates the RF source 10. After the RF source times out or after a temperature is sensed, the light and/or buzzer goes off. The user then raises the handle 14 and the carriage starts returning empty. This means that the connector stays mated. After ½ inch of travel, the lost motion linkage bottoms out and snaps the bag side pinch valve open thus causing liquid in the connector to be expelled into the bag side and not into the patient. The carriage continues back to the left releasing the sliding door. The user opens the door thus releasing the patient side pinch valve and opening the heater block. This then frees the connector for removal from the apparatus.

Having described one embodiment of the present invention, it should now be apparent to those skilled in the art that numerous other embodiments are contemplated as falling within the scope of this invention as defined by the appended claims.

What is claimed is:

1. In a system for infusing a liquid into a living body by means of a coupling that intercouples a conduit from a source of said liquid to a conduit implanted in said body, said coupling comprising, a hollow male member connected to one of said conduits and a hollow female member connected to the other of said conduits, said male and female members adapted to engage and said male member having a spike end entering said female member, said female member having an inner diameter along a section thereof greater than the diameter of the spike end so as to provide an annular space about the spike end to accommodate the liquid providing a reservoir change of liquid about the spike end capable of being heated for sterilization thereof, in combination with microwave heating means including a guided wave member encasing said coupling for providing heating of the charge of liquid, the combination of the heating and a clamping of the coupling to provide an isolated charge having a constant volume of liquid providing a pressure increase within the coupling that allows the liquid temperature to rise above the boiling point of the liquid.

2. In a system as set forth in claim 1 wherein said guided wave member comprises first and second members arranged to be removably closed around at least portions of said coupling.

3. In a system as set forth in claim 2 including first and second clamping means on opposite sides of said coupling and means to operate said clamping means to isolate the charge of said liquid within said coupling.

4. In a system as set forth in claim 3 wherein said means to operate includes means to release said clamping means.

5. In a system as set forth in claim 4 wherein the clamping means are released in sequence to first discharge any liquid into the source rather than body.

6. In a system as set forth in claim 5 including a housing for supporting the guided wave member and clamping means.

7. In a system as set forth in claim 6 wherein one of said first and second members is fixed in position in the housing while the other member is pivoted relative to the one member to open and close the guided wave member.

8. In a system as set forth in claim 7 including an operating handle to operate said clamping means.

9. In a system as set forth in claim 3 including a housing for supporting the guided wave member and clamping means.

10. In a system as set forth in claim 9 including a carriage in the housing for supporting one of the conduits and means for supporting the other conduit in a fixed position and means for operating the carriage to cause the conduits to be joined.

11. In a system as set forth in claim 10 wherein said coupling where the conduits are joined comprises an apertured member and cooperating hollow spike member adapted to engage with the apertured member.

12. In a system as set forth in claim 11 wherein said apertured member has an inner diameter along a section thereof greater than the diameter of the spike member so as to provide an annular space about the spike member to accommodate the liquid.

13. In a system for infusing a liquid into a living body by means of a coupling that intercouples a conduit from a source of said liquid to a conduit implanted in said body, apparatus for sterilizing said conduit coupling comprising, a guide wave member enclosing said coupling, means for clamping the conduits on opposite sides of said coupling to isolate a constant volume of a charge of liquid within said coupling and an electromagnetic energy source means for exciting said guided wave member to heat said charge of said liquid to an elevated temperature for a time long enough to destroy bacteria, the combination of said heating and clamping with a constant volume of liquid providing a pressure increase within the coupling that allows the liquid temperature to rise above the boiling point of the liquid, said guided wave member comprising first and second members arranged to be removably closed around at least portions of said coupling, first and second clamping means on opposite sides of said coupling and means to operate said clamping means to isolate the charge of liquid within said coupling, a housing for supporting said guided wave member and clamping means, a carriage in the housing for supporting one of the conduits, means for supporting the other conduit in a fixed position and means for operating the carriage to cause the conduits to be joined, said means for operating said carriage concurrently also operating said clamping means.

14. Method of infusing a liquid into a living body, in a process which requires the initial step of coupling a conduit from a source of said liquid to a conduit implanted in said body, comprising, following said coupling, the steps of holding an initial constant volume charge of said liquid in said conduits bridging the coupled ends of said conduit, heating said initial charge to an elevated temperature for a time long enough to destroy bacteria, the combination of said heating and clamping with a constant volume of liquid providing a pressure increase within the coupling that allows the liquid temperature to rise above the boiling point of the liquid and then releasing said liquid charge.

15. Method according to claim 14 including the step of temporarily fixing said coupled ends in a microwave heating enclosure and heating said initial charge in said enclosure.

* * * * *